(12) United States Patent
Bidet et al.

(10) Patent No.: US 9,132,949 B2
(45) Date of Patent: Sep. 15, 2015

(54) WORKSTATION AND METHOD FOR TRANSFERING BIOLOGICAL FLUID BETWEEN CONTAINERS

(75) Inventors: Francois Bidet, Bondues (FR); Roland Biset, Leuven (BE); Wilfried Mertens, Leuven (BE)

(73) Assignee: Terumo BCT, Inc., Lakewood, CO (US)

( * ) Notice: Subject to any disclaimer, the term of this patent is extended or adjusted under 35 U.S.C. 154(b) by 353 days.

(21) Appl. No.: 13/806,388

(22) PCT Filed: Jun. 21, 2011

(86) PCT No.: PCT/EP2011/060310
§ 371 (c)(1),
(2), (4) Date: Mar. 7, 2013

(87) PCT Pub. No.: WO2011/161090
PCT Pub. Date: Dec. 29, 2011

(65) Prior Publication Data
US 2013/0153047 A1 Jun. 20, 2013

(30) Foreign Application Priority Data

Jun. 22, 2010 (DE) .......................... 10 2010 030 371

(51) Int. Cl.
*B65D 79/00* (2006.01)
*A61J 1/10* (2006.01)
*G06F 19/00* (2011.01)
*A61M 1/02* (2006.01)
*A61M 1/36* (2006.01)

(52) U.S. Cl.
CPC . *B65D 79/00* (2013.01); *A61J 1/10* (2013.01); *A61M 1/02* (2013.01); *G06F 19/366* (2013.01); *A61J 2205/60* (2013.01); *A61M 1/0209* (2013.01); *A61M 1/0281* (2013.01); *A61M 1/3693* (2013.01); *A61M 2205/6054* (2013.01); *Y10T 137/0402* (2015.04); *Y10T 137/6851* (2015.04)

(58) Field of Classification Search
CPC ........ B65D 79/00; A61J 1/10; A61J 2205/60; G06F 19/366; A61M 1/02; A61M 1/0209; A61M 1/0281; A61M 1/3693; A61M 2205/6054
See application file for complete search history.

(56) References Cited

U.S. PATENT DOCUMENTS 7,776,601 B2 * 8/2010 De Gaulle et al. ................ 436/1
2003/0072676 A1 4/2003 Fletcher-Haynes et al.

FOREIGN PATENT DOCUMENTS

EP 1627651 B1 4/2012
FR 2825637 A1 12/2002

OTHER PUBLICATIONS

International Search Report, PCT/EP2011/060310, Oct. 5, 2011.
Notification of Transmittal of the International Preliminary Report on Patentability, PCT/EP2011/060310, Nov. 13, 2012.
Written Opinion of the International Searching Authority, PCT/EP2011/060310, Nov. 13, 2012.

* cited by examiner

*Primary Examiner* — Kristy A Haupt
(74) *Attorney, Agent, or Firm* — John R. Merkling

(57) ABSTRACT

The invention pertains to a method of connecting at least two containers for enabling a transfer of liquid from one container to the other container, comprising the steps of: a) Depositing a first cassette including at least a first container on a first tray. The first container has a plurality of connecting means. b) Depositing a second cassette including a second container on a second tray. The cassettes or the containers include a data storage means. c) The data are read by respective data reading means. d) The data are processed and it is verified whether they match each other. e1) In case of a negative result, the second cassette is removed and the steps from step b) onwards are repeated. e2) In case of a positive verification result, the containers are connected. f) Removing the second cassette. g) Repeating steps b) to f) a plurality of times.

7 Claims, 2 Drawing Sheets

WORKSTATION AND METHOD FOR TRANSFERING BIOLOGICAL FLUID BETWEEN CONTAINERS

Figure 1:
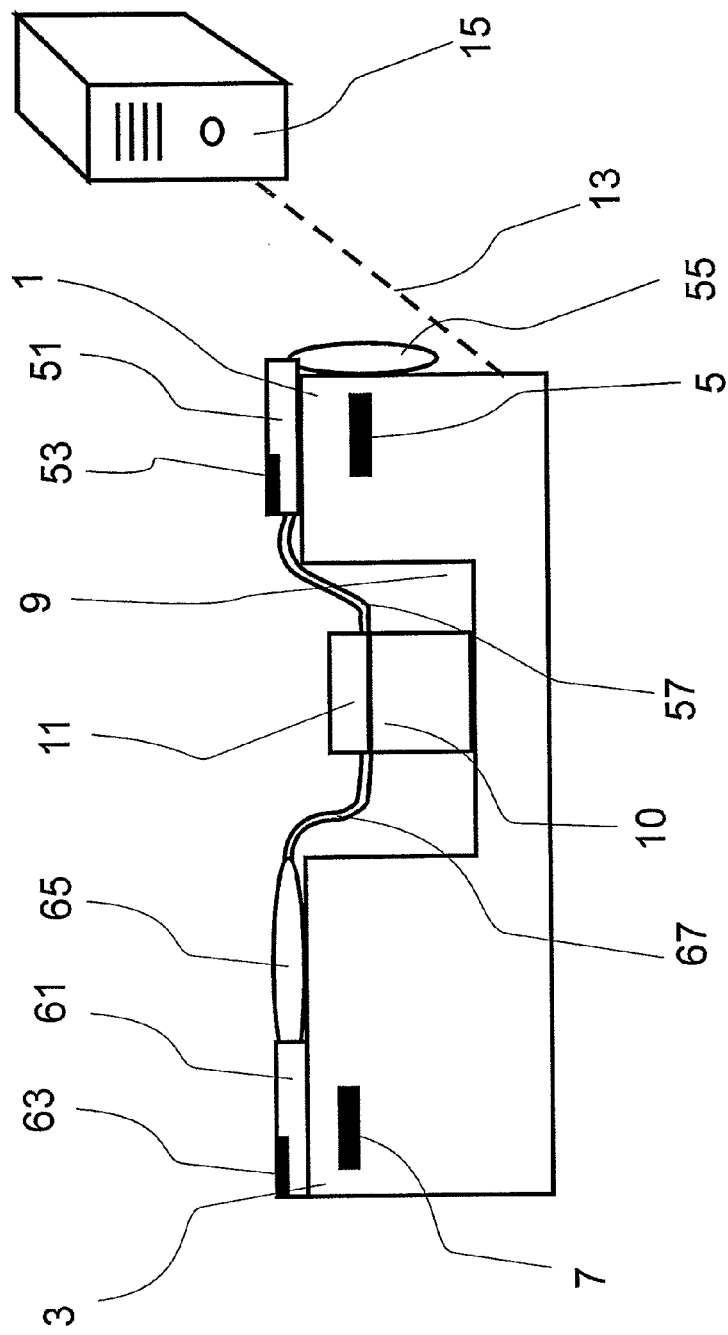

The invention pertains to a connection method and to a workstation suitable for performing the method. Especially, the connection method is for connecting two containers, at least one of which contains a liquid.

In transfusion medicine, since the beginning of the nineties, the so-called blood component therapy has been successful. This means that, instead of a whole unit of stored blood, a patient is only given the blood components he/she individually needs. This separate administration of the individual blood components makes it possible to optimally treat an average of 1.8 patients with one single unit of stored blood.

The essential blood components comprise the red blood corpuscles in the so-called erythrocyte concentrate that are transfused after a severe loss of blood to maintain the oxygen supply, the blood platelets in the thrombocyte concentrate that are administered in the event of coagulopathy (hemophilia) and the blood plasma that is administered in the event of coagulopathy and volume deficit. Apart from this, blood plasma is an essential basis for the production of numerous medicines.

The separation of the individual blood components, which is called cell harvesting, is known to be effected by the treatment of blood in a centrifuge. By centrifuging, the individual blood components are separated from each other and can, then, be separately filled into suitable containers and separately used.

In this connection, however, the assignment of the donor's data such as age, blood group, gender, etc. to the end product represents an essential problem. By a repeated transmission of these data, there is a great risk of an erroneous transmission, which might cause a wrong marking of the end product. A checking of the correct data transmission is only possible at a high expenditure or is even not possible at all.

Therefore, there is a need to create devices and methods ensuring a reliable data transmission over a plurality of processing steps.

The applicant has developed an internally known technology for ensuring a reliable data transmission over a plurality of method steps, as there are: a donation of the blood; transport of the blood; separating the blood into its components erythrocyte concentrate, plasma and buffy coat, for instance by a centrifugal process and transferring these components, i.e. blood products, into separate containers; marking the containers with the blood products.

However, when the separation process of the blood products is complete, a small amount of buffy coat remains in a container used for collecting and transporting the donated blood. Thus, a plurality of such small amounts of buffy coat usually occurring from different blood donors and/or donations is to be put together in order to economically enable further processes, such as the gaining of platelets or thrombocytes from the buffy coat. Generally, for this purpose, the buffy coats of different donors/donations are collected in a new container. In general, such a process is known as "buffy coat pooling". Therefore, the new container must repeatedly be connected with other containers containing buffy coat.

In this process an exact assignment and verification of the respective donor's and donation data is extremely important to avoid mixing of buffy coats not matching each other. For example, an important item is that the blood groups of the different donors match each other, while on the other hand the ages of the buffy coats also have to match each other. Accordingly, the date of the different donations must be within a certain range.

Thus, there is need for a method and device enabling a reliable data assignment and verification when connecting two containers.

According to the invention, a method of connecting at least two containers for enabling a transfer of liquid from one container to the other container comprises the steps of:

a) depositing a cassette including at least a first container on a first tray, wherein the first cassette or the first container includes a first data storage means, and the first container is in connection with an outer container;

b) depositing a second cassette including a second container filled with a liquid on a second tray, wherein the cassette or the container includes a second data storage means;

c) reading data from the first and second data storage means by first and second data reading means provided at the first and the second tray, respectively;

d) processing the data from the first and second data storage means by a controller and verifying whether the data from the first and second data storage means match each other;

e1) in case of a negative verification result, informing the user, and then removing the second cassette including the second container and repeating the steps from step b) onwards;

e2) in case of a positive verification result, connecting the first container and the second container;

f) removing the second cassette including the second container from the second tray;

g) repeating steps b) to f) a plurality of times such that a plurality of second containers is connected with the first container;

h) transferring the liquids from the plurality of second containers to the first container;

i) separating the plurality of second containers from the first container.

Since the cassettes or the containers attached to the cassettes include a data storage device, it is definitely ensured that the data on the respective data storage device corresponds to the contents of the container. In the case of the second cassette, this means that it is verified whether the liquid in the second container matches with the liquid in the first container and with the liquids in the second containers previously connected to the first container. For instance, in the case of buffy coat pooling, it may be verified whether the blood groups match each other or whether the ages of the buffy coats match each other.

After the connection method is finished, a number of buffy coats corresponding to the repeated performances of the method can be collected in the first container. However, if there are not sufficient numbers of buffy coats matching each other, also the first cassette and container connected with merely some second containers can be removed after step f) and stored for a certain time until the buffy coat supply is resumed.

In this case, data concerning the new contents of the first container can be written on the first data storing means before the removal of the cassette. Alternatively, however, instead of writing new data into the first data storing means, the ID-number of the first cassette as well as its contents can be stored by the controller in a memory provided at a work station used for performing the method or instance at an external server. Thus, when resuming the method at a later date, verification of the data of the then new second data storage means with the stored data is possible.

Preferably, the first and second data storage means can be provided in the form of first and second RFID-tags, and the data reading means are first and second RFID-readers, respectively. Additionally or alternatively, the data storage means are provided in the forms of first and/or second labels, the data being printed in the form of first and/or second bar codes or real text. In such a case, the data reading means are solely or additionally provided in the form of first and/or second bar code readers and/or text readers.

Advantageously, the liquid transferred can be a buffy coat remaining from a blood cell gaining process.

Advantageously, a data communication line to a central server can be established and the controller can be provided with the central server.

Advantageously, the connecting means can be provided with the first and the second container in the form of tubes, and step e2) can be performed by cutting and then hot melting two tubes, i.e. one tube of each container, together. The cutting and hot melting enables a sterile connection of the two containers without risking contamination.

Advantageously, for transferring the liquid, which is preferably done after the whole plurality of second containers is connected to the first container, the second containers can be arranged above the first container such that the liquid can be transferred by gravity.

Advantageously, data concerning the method steps and/or the contents of the containers can be written into the first and/or the second data storage means. For instance, the number of repetitions of the method, the blood groups of the donors, the dates of the donations and other data can be written into the first data storage means. Also an ID-number of the first data storage means can be written into the second data storage means. Preferably, the data writing means are provided in the form of RFID-writers. However, data can be also printed, e.g. on labels by printers in the form of bar codes and/or text.

Furthermore, according to the invention, a workstation for connecting at least two containers for enabling a transfer of liquid from one container to the other container comprises a first tray for depositing a first cassette including a first data storage means and at least a first container; a second tray for depositing a second cassette including a second data storage means and a second container; first and second data reading means for reading the data of the first and second data storage means, respectively; a connection device for connecting the first container and the second container.

Such a workstation is suitable for performing the method according to the invention.

The workstation may further comprise a controller and/or a communication means for communicating with a central server.

This enables a data exchange with e.g. the central server of a blood bank in order to learn which kinds of products are required.

Furthermore, the workstation may comprise writing means for writing data into the first and/or second data storage means. Thus, an update of the stored information is possible any time, e.g. in a case where the process is interrupted to be continued at a later stage.

Advantageously, the connecting means may comprise cutting means and hot melting means for cutting and hot melting tubes. Furthermore, the first and second data reading means may be provided in the form of respective RFID-readers and/or in the form of respective bar code readers and/or the data writing means may be provided in the form of one or more RFID-writers, and/or one or more bar code printers and/or one or more text printers, the printers being capable of printing on labels to be put on the first or second containers.

Figure 2:
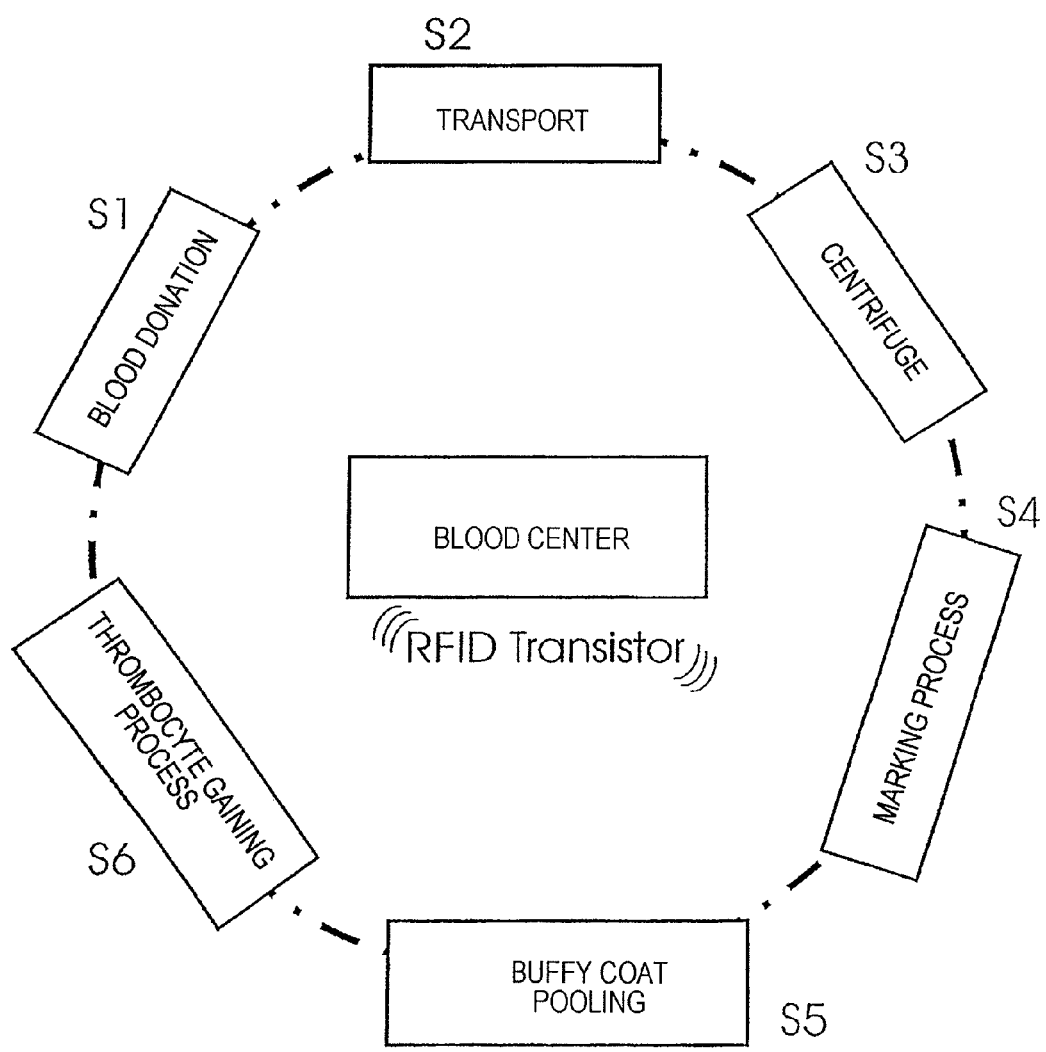

Further advantages of the invention will be seen from the description of a presently preferred embodiment together with the figures, in which:

FIG. 1 shows a schematic view of a workstation of a presently preferred embodiment, FIG. 2 shows a schematic diagram for understanding the advantages of the invention.

The method of connecting at least two containers as well as a workstation according to a presently preferred embodiment will be described on the basis of FIG. 1.

The workstation comprises a first tray 1 and a second tray 3. Respective RFID-readers/RFID-writers 5 and 7 are assigned to each of the trays. An accommodation chamber 9 is provided between the two trays 1, 3. Furthermore, in the accommodation chamber 9, a combined cutting and hot melting device 10 having a lid 11 is provided.

Via a data communication line 13, data from the RFID-readers/RFID-writers 5, 7 can be transferred to a server 15. In the server, there is a control unit for processing the data.

For performing the method of the invention, a user puts a first cassette 51 including a RFID-tag 53 serving as first data storage means according to the invention onto the tray 1. A pooling bag 55 serving as first container according to the invention, which is filled with preservation liquid, is fixedly attached to the cassette 1. A plurality of tubes 57, only one of which is shown in FIG. 1, is connected to the pooling bag 55. The pooling bag 55 is put to hang downwards from the tray 1. One of the tubes 57 assigned to the pooling bag 55 is inserted into a receiving groove of the cutting and hot melting device 10. Furthermore, a product bag not shown in FIG. 1 is connected with the pooling bag 55 via another tube, which is not shown either. The connection between the pooling bag 55 and the product bag is interrupted by a clamp.

Then, in a similar manner, a cassette 61 including a RFID-tag 63 serving as second data storage means according to the invention is put on the tray 3. A donation bag 65 containing buffy coat having remained from a blood cell gaining process is fixedly attached to the cassette 61.

The buffy coat is the remainder of a blood cell gaining process in which a separation of the blood components erythrocyte concentrate, plasma and buffy coat took place in a centrifuge. Then, the first two components were transferred to product bags connected to the donation bag 65, while the buffy coat remained in the donation bag. After the transfer, the product bags containing the plasma and the erythrocyte concentrate, respectively, were separated from the donation bag to be individually further processed.

The donation bag 65 containing the buffy coat is placed on the tray 3. Thus, there is a height difference between the pooling bag 55 and the donation bag 65.

A tube 67 connected to the donation bag 65, however, is also inserted in a respective accommodation groove of the cutting and hot melting device 10.

Thereafter, the lid 11 of the cutting and hot melting device 10 is closed, thus fixing the tubes. In order to be able to close properly, there are corresponding recesses provided in the lid 11, which fit the shape of the tube 67 as well as that of the tube 57.

After the above described preparations are performed, the user presses a start button provided at the workstation.

Subsequently, the RFID-reader 5 and the RFID-reader 7 read the data stored on the RFID-tags 53 and 63, respectively. Via the communication line 13, the data are sent to the server 15 where a control unit verifies whether the data match each other. The data used for the verification can comprise the blood group and other personal data of the donor, the date of the donation, the ID-numbers of the cassettes 51 and 61, and others.

If the data verification is positive, the control unit accordingly informs the cutting and hot melting device 10. The cutting and hot melting device 10 then starts the connection process of the two tubes 57 and 67, in which the ends of the two tubes 57 and 67 are opened, e.g. by cutting them off, and are then hot melted together.

The RFID-reader/RFID-writers 5 and 7 then accordingly alter the data stored in the RFID-tags 53 and 63 to reflect the current situation. That is, the memory of RFID-tag 53 then contains the additional information concerning the connected container 65, as well as the data concerning the donor, the donation, etc. Thereafter, the cassette 61 is removed and replaced by a new cassette 61 for the process to be repeated 2 to 8 times until each of the plurality of tubes 57 of the pooling bag 55 is connected with one tube 67 of respective donation bags 65 attached to respective cassettes 61.

It is to be noted that, if there is no sufficient supply of donation bags containing the buffy coat, the connection process can be interrupted by removing the cassette 51 together with the then attached second cassettes 61 including respective donation bags 65. In this case the cassette 51 and the cassettes 61 can be stored to be used again, after the shortage of the required buffy coat is overcome.

When again taking up the pooling process with the cassette 51, a reliable determination and verification whether the then new buffy coat matches the one already present with the pooling bag can be made since the data are stored on the RFID-tag 53.

Following the connection process, that is, when all tubes 57 are connected to respective tubes 67 of donation bags 65, all of the donation bags 65 are put in a position above the pooling bag 55. Thereafter, the transfer of the buffy coats present in the plurality of donation bags 65 is started, e.g. by opening respective clamps provided on the tubes 67 and 57.

Thereafter, due to the height difference of the pooling bag 55 and the donation bags 65, the buffy coats in the donation bags 65 flow into the pooling bag 55 via the tubes 67 and 57. Then, the connection between the plurality of tubes 57 and the respective tubes 67 is again cut and the then open ends of the tubes 57 are fluid- and air-tightly sealed.

After it is completely filled, the cassette 51 together with the pooling bag 55 is brought to another centrifugal process in which the platelets/thrombocytes contained in the buffy coats are gained. Since the cassette 51 including the RFID-tag 53 serves as data transporter, a reliable assignation of the data to the product is possible also in the oncoming processing step.

FIG. 2 shows a schematic diagram for understanding the advantages of the invention. That is, throughout the whole process, the donated blood is accompanied by the cassettes having the RFID-tags. That is, at the blood donation center, the donor's data are written onto the RFID-tag. Then, the donor receives the cassette having the donation bag attached thereto. Via tubes, product bags are also in connection with the donation bag, however the connection is interrupted by clamps (Step S1).

After the donation, the whole set is transported to a blood center for the further processing (S2). There, the cassette with the donation bag and the product bags is put into an insert of a centrifuge. Thereafter, a centrifugal process for separating the erythrocyte concentrate, the plasma and the buffy coat will take place (S3).

After the centrifugal process, the insert together with the bags is inserted into a slot of a workstation for marking process (S4). Having separated and sealed the product bags at the marking workstation, the cassette, together with the donation bag comprising the buffy coat, is brought to the buffy coat pooling process (S5) in which buffy coats of different donors are put together for further processing, as is herein described. Due to the RFID tags attached to the respective cassettes, it can be verified in this process whether the plural buffy coats used in the process match each other. After the buffy coat pooling, the obtained buffy coat liquid is brought to a thrombocyte gaining process (S6), where thrombocytes are extracted from the buffy coat liquid.

Alternatively to the described embodiment, the following modifications of the invention are possible.

While it is described that the altered data are written onto the RFID-tags provided on the respective cassettes, the data can alternatively be stored in a memory of the server. In such a case, merely the ID-number of the respective cassette is read from the RFID-readers and the data concerning the respective cassette is taken from the memory.

Instead of providing the RFID-tag on the cassette, it can be provided on the donation bag or on the pooling bag, respectively. The important issue is that the RFID-tag cannot be separated from the contents of the bag in order to ensure the correct data assignment throughout all processes including preceding and succeeding processes.

The data connection line can be established via wire, WLAN, UMTS, Bluetooth or others.

Instead of using gravity for the transfer of the buffy coat, the buffy coat can be transferred by inserting the donation bag into a squeezing device and squeezing it.

Instead of using bags, other suitable containers such as bottles may be used. However, using bags is advantageous, especially since they can be provided in an evacuated state. Thus, handling liquids is facilitated.

Instead of using a plurality of tubes with the pooling bag, there can be one tube provided at the pooling bag which later branches into the plurality of tubes. Such an arrangement advantageously facilitates the separation of the tubes after the pooling process is completed.

The scope of protection of the invention is defined exclusively by the attached claims.

The invention claimed is:

1. A method of connecting at least two containers for enabling a transfer of liquid from one container to the other container, comprising the steps of:
   a) depositing a first cassette (51) including at least a first container (55) on a first tray (1), wherein the first cassette (51) or the first container (55) includes a first data storage means (53), and the first container (55) is in connection with an outer container, the first container (55) having a plurality of connecting means (57);
   b) depositing a second cassette (61) including a second container (65) filled with a liquid on a second tray (3), wherein the second cassette (61) or the second container (65) includes a second data storage means (63);
   c) reading data from the first and second data storage means (53, 63) by first and second data reading means (5, 7) provided at the first and the second tray (1, 3), respectively;
   d) processing the data from the first and second data storage means (53, 63) by a controller and verifying whether the data from the first and second data storage means (53, 63) match each other;
   e1) in case of a negative verification result, informing the user, and then removing the second cassette (61) including the second container (65) and repeating the steps from step b) onwards;

e2) in case of a positive verification result, connecting the first container (55) and the second container (65);

f) removing the second cassette (61) including the second container (65) from the second tray (3);

g) repeating steps b) to f) a plurality of times such that a plurality of second containers (65) is connected with the first container (55);

h) transferring the liquids from the plurality of second containers (65) to the first container (55);

i) separating the plurality of second containers (65) from the first container (55).

2. The method of connecting at least two containers according to claim 1, wherein the first and second data storage means are provided in the form of first and second RFID-tags (53, 63), and the data reading means are first and second RFID-readers (5, 7), respectively, and/or the data storage means are provided in the forms of first and/or second labels, the data being printed in the form of first and/or second bar codes and/or first and/or second texts, and/or the data reading means are provided in the form of first and/or second bar code readers and/or first and/or second text readers.

3. The method of connecting at least two containers according to claim 1, wherein the liquid transferred is a buffy coat remaining from a blood cell gaining process.

4. The method of connecting at least two containers according to claim 1, wherein a data communication line (13) to a central server (15) is established and the controller is provided with the central server (15).

5. The method of connecting at least two containers according to claim 1, wherein the connecting means are provided in the form of tubes (57, 67) with the first and the second container (55, 65), and step e2) is performed by cutting and then hot melting a respective tube (57) of the first container (55) and the tube (67) of respective second container (65) together.

6. The method of connecting at least two containers according to claim 1, wherein the plurality of second containers (65) is arranged above the first container (55) such that the liquid is transferred by gravity.

7. The method of connecting at least two containers according to claim 1, wherein data concerning the method is written into the first and/or the second data storage (53, 63) means by respective RFID-writers (5, 7) and/or is printed onto respective labels by a printer.

\* \* \* \* \*